United States Patent
Weber

(10) Patent No.: US 7,316,771 B2
(45) Date of Patent: Jan. 8, 2008

(54) MEDIUM FOR ANALYTIC AND PREPARATIVE ELECTROPHORESIS

(75) Inventor: Gerhard Weber, Kirchheim (DE)

(73) Assignee: Becton, Dickinson and Company, Franklin Lakes, NJ (US)

(*) Notice: Subject to any disclaimer, the term of this patent is extended or adjusted under 35 U.S.C. 154(b) by 650 days.

(21) Appl. No.: 10/381,029

(22) PCT Filed: Aug. 30, 2001

(86) PCT No.: PCT/EP01/10036

§ 371 (c)(1),
(2), (4) Date: Apr. 1, 2003

(87) PCT Pub. No.: WO02/25263

PCT Pub. Date: Mar. 28, 2002

(65) Prior Publication Data

US 2004/0101973 A1    May 27, 2004

(30) Foreign Application Priority Data

Sep. 21, 2000   (DE)   ................ 100 47 088

(51) Int. Cl.
*G01N 27/26* (2006.01)
(52) U.S. Cl. ............... 204/459; 204/548; 204/610; 204/644
(58) Field of Classification Search ........ 204/450–470, 204/548, 600–621, 644
See application file for complete search history.

(56) References Cited

U.S. PATENT DOCUMENTS

| | | |
|---|---|---|
| 2,555,487 A | 6/1951 | Haugaard et al. |
| 2,878,178 A | 3/1959 | Bier |
| 3,085,956 A | 4/1963 | Caplan |
| 3,125,500 A | 3/1964 | Grossman et al. |
| 3,140,714 A | 7/1964 | Murphy et al. |
| 3,149,060 A | 9/1964 | Dobry et al. |
| 3,287,244 A | 11/1966 | Mel |
| 3,320,148 A | 5/1967 | Skeggs |

(Continued)

FOREIGN PATENT DOCUMENTS

EP    0081375 B1    4/1989

(Continued)

OTHER PUBLICATIONS

Weber, Gerhard et al, "Recent developments in preparative free flow isoelectric focusing." Electrophoresis. 19, 1649-1653. (1998).*

(Continued)

*Primary Examiner*—Nam Nguyen
*Assistant Examiner*—Jeffrey Barton
(74) *Attorney, Agent, or Firm*—Mark Lindsey

(57) ABSTRACT

The invention relates to a medium for analytic and preparative electrophoresis which includes a content of acids and bases of different pKa values. The medium contains at least two acids, where the difference in pKa values (ΔpKa) of adjacent acids are no greater than 1.0, preferably in the range from 0.8 to 0.5. The medium also contains at least two bases, whose pKa values range from approximately 1.5 to 11, and the difference of the pKa values (ΔpKa) of adjacent bases is no greater than 1.0, preferably in the range from 0.8 to 0.5.

15 Claims, 1 Drawing Sheet

U.S. PATENT DOCUMENTS

| | | |
|---|---|---|
| 3,320,149 A | 5/1967 | Israeli |
| 3,412,007 A | 11/1968 | Strickler |
| 3,412,008 A | 11/1968 | Strickler |
| 3,458,427 A | 7/1969 | Strickler |
| 3,458,428 A | 7/1969 | Huebner |
| 3,498,905 A | 3/1970 | Strickler |
| 3,509,035 A | 4/1970 | Huebner |
| 3,519,549 A | 7/1970 | Grassman et al. |
| 3,616,455 A | 10/1971 | Von Munchhausen |
| 3,655,541 A | 4/1972 | Strickler |
| 3,663,395 A | 5/1972 | Strickler |
| 3,668,107 A | 6/1972 | Lappe |
| 3,755,132 A | 8/1973 | Kolin et al. |
| 3,758,395 A | 9/1973 | Strickler |
| 3,766,047 A | 10/1973 | Elevitch |
| 3,821,102 A | 6/1974 | Fletcher et al. |
| 3,847,773 A | 11/1974 | Snyder |
| 3,989,613 A | 11/1976 | Gritzner |
| 4,043,895 A | 8/1977 | Gritzner |
| 4,061,560 A | 12/1977 | Hannig et al. |
| 4,107,027 A | 8/1978 | Mückenmuller et al. |
| 4,139,440 A | 2/1979 | Chrambach et al. |
| 4,141,809 A | 2/1979 | Aitchison et al. |
| 4,204,929 A | 5/1980 | Bier |
| 4,214,981 A | 7/1980 | Giddings |
| 4,279,724 A | 7/1981 | Hearn et al. |
| 4,310,408 A | 1/1982 | Rose et al. |
| 4,334,972 A | 6/1982 | Soederberg |
| 4,358,358 A | 11/1982 | Rhodes |
| 4,362,612 A | 12/1982 | Bier |
| 4,383,905 A | 5/1983 | Richman |
| 4,394,246 A | 7/1983 | Richman et al. |
| 4,440,638 A | 4/1984 | Judy et al. |
| 4,465,582 A | 8/1984 | Richman |
| 4,749,458 A | 6/1988 | Muroi et al. |
| 4,874,507 A | 10/1989 | Whitlock |
| 4,897,169 A | 1/1990 | Bier et al. |
| 5,032,247 A | 7/1991 | Tarnopolsky |
| 5,071,536 A | 12/1991 | Ivory |
| 5,087,338 A | 2/1992 | Perry et al. |
| 5,131,994 A | 7/1992 | Shmidt et al. |
| 5,133,844 A | 7/1992 | Stevens |
| 5,180,480 A | 1/1993 | Manz |
| 5,277,774 A | 1/1994 | Shmidt et al. |
| 5,336,387 A | 8/1994 | Egen et al. |
| 5,439,571 A | 8/1995 | Sammons et al. |
| 5,447,612 A | 9/1995 | Bier et al. |
| 5,540,826 A | 7/1996 | Bier et al. |
| 5,562,812 A | 10/1996 | Carlson et al. |
| 5,817,225 A | 10/1998 | Hinton |
| 5,906,724 A | 5/1999 | Sammons et al. |
| 5,972,190 A | 10/1999 | Richman |
| 6,210,574 B1 | 4/2001 | Sammons et al. |
| 6,328,868 B1 | 12/2001 | Weber |
| 6,749,733 B1 | 6/2004 | Sibbett |
| 6,758,953 B2 | 7/2004 | Thomas et al. |
| 6,793,791 B2 | 9/2004 | Bier |
| 2001/0040095 A1 | 11/2001 | Shimizu et al. |
| 2001/0040096 A1 | 11/2001 | Yamamoto et al. |
| 2002/0008027 A1 | 1/2002 | Rhodes et al. |
| 2004/0031683 A1 | 2/2004 | Eipel et al. |
| 2004/0045826 A1 | 3/2004 | Weber |
| 2004/0050697 A1 | 3/2004 | Eckerskorn et al. |
| 2004/0050698 A1 | 3/2004 | Eckerskorn et al. |
| 2004/0163956 A1 | 8/2004 | Bier |

FOREIGN PATENT DOCUMENTS

| | | |
|---|---|---|
| JP | 061095241 A | 5/1986 |
| JP | 061162741 A | 7/1986 |
| JP | 061215952 A | 9/1986 |
| JP | 061215953 A | 9/1986 |
| JP | 063067557 A | 3/1988 |
| JP | 063117252 A | 5/1988 |
| JP | 06130035 A | 5/1994 |
| JP | 2001091497 A | 4/2001 |
| JP | 2001153841 A | 6/2001 |
| JP | 2003247980 A | 9/2003 |
| JP | 2004113079 A | 4/2004 |
| WO | 9110129 | 7/1991 |
| WO | 04077039 | 9/2004 |

OTHER PUBLICATIONS

Bade, Andreas, "Untersuchungen zu Funktion und Eigenschaften einer Phospholipase aus Soja (Glycine Max)", Dissertation published 2003. (134 pages).*

Babel Fish Translation of Section 2.4.2 of Bade's dissertation, service available at http://babelfish.altavista.com/tr. (1 page).*

Z. Buzas et al, "Formation of natural pH gradients in sequential moving boundary systems with solvent counterions II. Predicted and experimantal properties", Electrophoresis, 4, 27-35. (1983).*

* cited by examiner

MEDIUM FOR ANALYTIC AND PREPARATIVE ELECTROPHORESIS

This application is a 371 of International Application No. PCT/EP01/10036, filed 30 Aug. 2001, and claims benefit of foreign priority to German Application No. DE 100 47 088.2, filed 21 Sep. 2000.

BACKGROUND OF THE INVENTION

1. Field of the Invention

This present invention concerns a medium for analytical and preparative electrophoresis.

2. Description of Related Art

Such aqueous solutions, which form a pH gradient upon high-voltage electrophoresis, are used on a large scale to analyze proteins and peptides. Such prior art solutions contain polyelectrolytes with amphoteric properties and are usually manufactured synthetically by means of condensation and/or polymerization of polyamines with unsaturated carboxylic acids. As a result of such synthesis, many different compounds with different molecular weights and a varying number of acid groups (carboxylic groups) and basic groups (amino and/or imino groups) are produced. Under the conditions prevalent during high-voltage electrophoresis, these polyelectrolytes arrange themselves, due to the different ratio between acidic and basic groups, in such a way that polyelectrolytes with particularly acidic properties concentrate in the proximity of the anode, and all other polyelectrolytes are arranged, in accordance with the "ranking" of acidic and basic properties, between the electrodes and are also concentrated in the process. By the selective accumulation of polyelectrolytes in accordance with the acidic and/or basic properties of the individual species, a pH gradient is produced throughout the entire aqueous solution.

By means of this pH gradient, amphoteric compounds such as proteins and peptides can be separated in accordance with the different acidic and/or basic properties. This analytical separation procedure is referred to in the literature as "isoelectric focusing". In the situation where this procedure is carried out in a special gel (polyacrylamide), this procedure is referred to as PAGIEF (polyacrylamide isoelectric focusing). PAGIEF is considered the standard procedure.

There are a number of reported disadvantages when using the commercially available ampholytes. For example, the unsaturated acids that are used in the synthesis of commercially available ampholytes, e.g. substituted acrylic acids, are highly toxic. Their residual content is considered to represent a significant hazard. For that reason, the use of commercially available ampholytes for the cleaning of proteins for subsequent use in human applications is prohibited.

Additionally, during ampholyte synthesis, a large number of chemical species of unknown structure is formed whose relative concentration may vary significantly across batches. This has an adverse impact on the reproducibility of analytical results. In certain applications, "artificial bands" are reported as a result of undesired complex formation between the ampholyte and the analyte.

It has also been reported that partial interference with the analytical color reaction of proteins occurs which is caused by ampholytes with a higher molecular weight. Further, an unusually high percentage of ampholytes with a molecular weight>10 KD in products of certain manufacturers has been reported on several occasions. In the case of preparative cleaning of proteins, the subsequent separation of the ampholyte is difficult and sometimes incomplete; the suspected cause is complex formation. Finally, commercial ampholytes have been found to be unsuitable for use as separating media for bioparticles, considering that bioparticles aggregate in these media.

SUMMARY OF THE INVENTION

The object of this invention is to provide aqueous solutions for isoelectric focusing (IF) which contain acids and bases with different pKa values which are not subject to the above-mentioned disadvantages and whose range of applications is therefore significantly wider. These objects are achieved by an aqueous solution medium for analytical and preparative electrophoresis containing acids and bases with different pKa values, characterized in that the medium contains at least two acids whose pKa values are between approx. 3.0 and 12. Further, the difference of the pKa values ($\Delta$pKa) of neighboring acids is not larger than 1, and preferably between 0.8 and 0.5, and the medium contains at least two bases whose pKa values are between approx. 1.5 and 11, where the difference between the pKa values ($\Delta$pKa) of neighboring bases is not larger than 1, and preferably between 0.8 and 0.5.

Specifically, the aqueous solution medium in accordance with this invention contains a mixture of acids and bases with graded "acidity" and/or "basicity" levels. The pKa values of the individual acids vary between pKa 3.5 to pKa 12, and the differences of the pKa values ($\Delta$pKa) of the "neighboring" acids should not exceed $\Delta$pKa=1. A value of $\Delta$pKa of less than 0.8 is considered ideal. The pKa values of the bases used vary between pKa=1.5 and pKa=11. The differences between the values of the individual bases are ideal in case $\Delta$pKa<0.8 is fulfilled.

The number of acids and/or bases used and their relative concentrations determine the range and the profile of the pH gradient. The minimum number is 2 acids and/or 2 bases each, and 3 acids and/or 3 bases are preferred. In the case of a wide pH range (pH 2.5 to 10), 11 acids and 13 bases with graded pKa values are used.

DETAILED DESCRIPTION OF THE INVENTION

Figure 1:
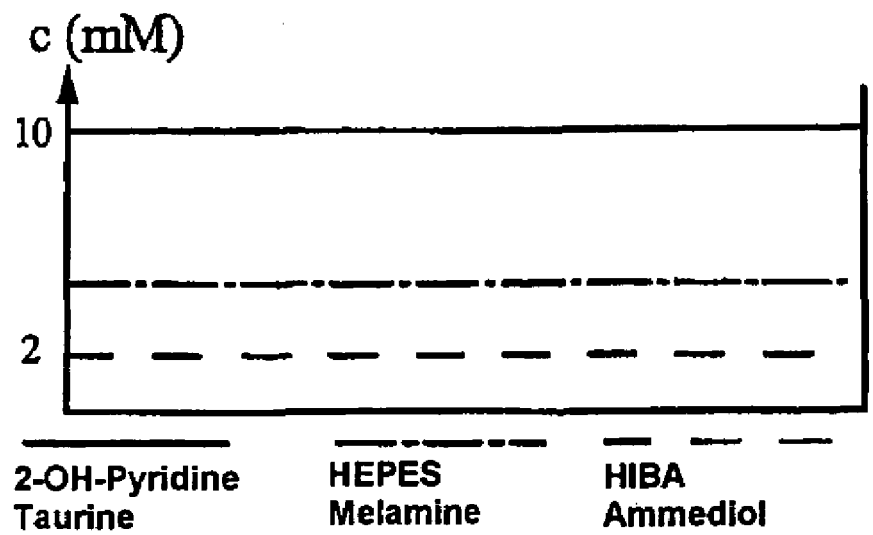
FIG. 1 provides a graphical illustration of the concentrations of typical acids and bases.
Figure 2:
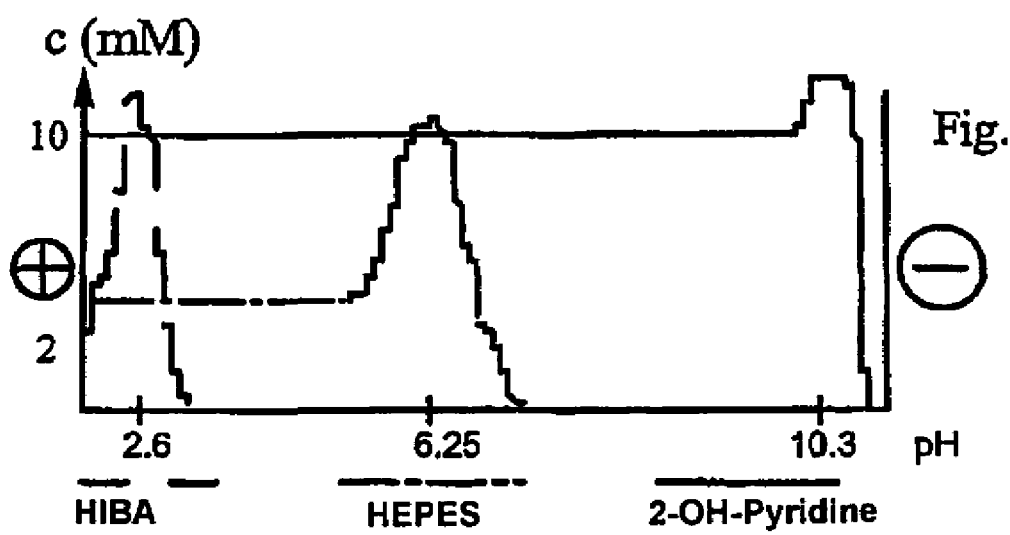
FIG. 2, graphically illustrates the relative concentrations of typical acids after electrophoretic migration.
Figure 3:
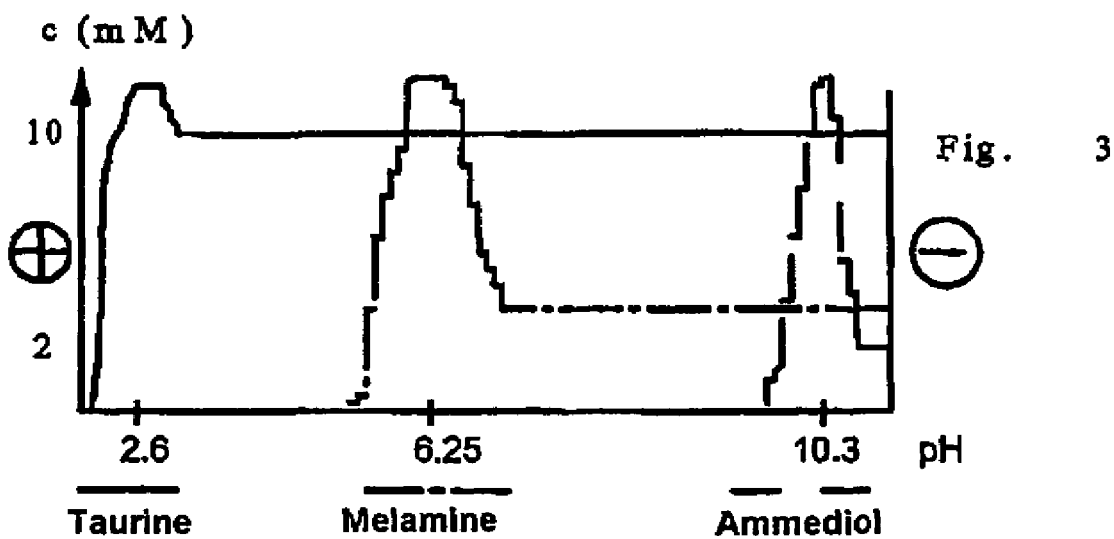
FIG. 3, graphically illustrates the relative concentrations of typical bases after electrophoretic migration.

FIGS. 1 through 3, use a model of three typical acids and bases each to depict the electrophoretic migration and the resulting establishment of the pH gradient. Different concentrations of the acids hydroxyl butyric acid (HIBA: pKa=3.8), HEPES (pKa=7.5), and 2-hydroxy pyridine (pKa=11.6), and the bases taurine (pKa=1.5), melamine (pKa=5), and ammediol (pKa=9) are contained in the original solution (see FIG. 1). As a general rule, the relative concentrations of both very weak acids and very weak bases are significantly higher compared with the concentrations of the relatively strong acids and bases (approximately by a factor of five). The concentrations of acids and basis of "moderate" strength are increased by a factor of approx. 1.5 to a maximum of 3.

FIGS. 2 and 3 show the relative concentrations of the above-described acids and bases after electrophoretic migration. In the "state of equilibrium" shown herein, "pairs" of acids and bases are formed which may only ionize each other to a very limited degree (strong acid: HIBA and very weak base: taurine, weak acid: HEPES and weak base: melamine, and strong base: ammediol and very weak acid: 2OH pyridine), and as a result of thereof, the electrophoretic migration of the media's own substances comes to a stop. In the area of these pairs, a pH value is produced which corresponds to the arithmetic mean of the pKa values of the acid and of the base. The pH values of these pairs are therefore as follows: HIBA/taurine solution, pH=2.6; HEPES/melamine, pH=6.25; 2-OH pyridine/ammediol, pH=10.3. The pH range over which a pair is able to ensure a stable pH value is approximately one pH unit. All other acids and bases with different pKa values form pairs which also ensure a stable pH value within one pH unit as long as the absolute concentrations of the individual acids and bases guarantee sufficient buffer capacity in the state of equilibrium.

The solutions in accordance with this invention include well-defined chemicals whose properties are known in detail. The reproducibility of the entire mixture is ensured by the precision and/or accuracy of the scale used in its production. Each of the substances used are non-toxic, and each of the substances used is "monofunctional", i.e. effects such as complex formation and/or biopolymer aggregation either do not occur at all or are at least significantly reduced compared with polyelectrolytes comprising several functional groups. The molecular weight of all individual species of the mixture is <300 Dalton.

The aqueous solutions in accordance with this invention have already been successfully tested as separating media for biopolymers and bioparticles and have been found to be biocompatible. Considering that most individual species can be substituted by chemicals with similar pKa values, the special requirements of bioparticles in terms of separating media can be taken into account by changing the composition of the mixture. For the above reasons, official approval of such solutions for use in the cleaning of bioparticles and biopolymers (peptides and proteins) for subsequent application in humans appears is possible.

Below, several examples of aqueous solutions in accordance with this invention with different pH intervals are presented. Please note that, during the manufacture of a medium for a narrower pH interval, the absolute concentrations of acids and bases are increased; usually, the differences in the pKa values are also reduced by using new constituents.

EXAMPLE 1

(pH Interval 3-10)

| Acid | pKa | c (mMol) | Base | pKa | c (mMol) |
|---|---|---|---|---|---|
| Hydroxy-Isobutyric Acid | 4.0 | 1.5 | Betaine | 1.8 | 10 |
| Pivalic Acid | 5.0 | 5.0 | 2-Amino Butyric Acid | 2.3 | 10 |
| Picolinic Acid | 5.5 | 2 | Creatine | 2.7 | 10 |
| MES | 6.1 | 4 | Nicotinic Acid Amide | 3.1 | 8 |
| MOPSO | 6.9 | 2 | Pip-4-Carboxylic Acid | 3.5 | 3 |

-continued

| Acid | pKa | c (mMol) | Base | pKa | c (mMol) |
|---|---|---|---|---|---|
| HEPES | 7.5 | 2 | EACA | 4.4 | 2 |
| EPPS | 8.0 | 2 | Melamine | 5.0 | 2 |
| TAPS | 8.3 | 3 | Hydroxyethyl Pyridine | 5.3 | 2 |
| | | | Histidine | 6.0 | 3 |
| AMPSO | 9.0 | 6 | BISTRIS | 6.5 | 3 |
| | | | Hydroxyethl | | |
| CAPSO | 9.6 | 8 | Morpholine | 7.1 | 3 |
| CAPS | 10.3 | 9 | Triethanol Amine | 7.8 | 2 |
| CABS | 10.8 | 10 | TRIS | 8.3 | 2 |
| 2-Hydroxy-Pyridine | 11.8 | 10 | Ammediol | 9.0 | 2 |

EXAMPLE 2

(pH Interval 4-6)

| Acid | pKa | c (mMol) | Base | pKa | c (mMol) |
|---|---|---|---|---|---|
| Pivalic Acid | 5.0 | 5 | Creatine | 2.7 | 30 |
| Picolinic Acid | 5.5 | 10 | Glycl Glycine | 3.1 | 20 |
| MES | 6.1 | 20 | Pip.-4-Carboxylic Acid | 3.5 | 10 |
| MOPSO | 6.9 | 30 | GABA | 4.2 | 10 |
| | | | EACA | 4.4 | 5 |

EXAMPLE 3

(pH Interval 5.5-7.5)

| Acid | pKa | c (mMol) | Base | pKa | c (mMol) |
|---|---|---|---|---|---|
| MOPSO | 6.9 | 10 | EACA | 4.4 | 15 |
| MOPS | 7.2 | 10 | Creatinine | 4.8 | 15 |
| HEPES | 7.5 | 15 | Hydroxyethyl Pyridine | 5.4 | 10 |
| EPPS | 8.0 | 15 | β-Picoline | 5.8 | 10 |
| TAPS | 8.3 | 20 | BISTRIS | 6.5 | 5 |

EXAMPLE 4

(pH Interval 8-11.5)

| Acid | pKa | C (mMol) | Base | pKa | c (mMol) |
|---|---|---|---|---|---|
| TAPS | 8.3 | 3 | Imidazol | 7.0 | 15 |
| AMPSO | 9.0 | 5 | Triethanol Amine | 7.8 | 12.5 |
| CAPSO | 9.6 | 7.5 | TRIS | 8.3 | 12.5 |
| GABA | 10.2 | 10 | Ammediol Hydroxy Ethyl | 8.8 | 10 |
| EACA | 10.6 | 10 | Ethylene Diamine | 9.8 | 7.5 |

-continued

| Acid | pKa | C (mMol) | Base | pKa | c (mMol) |
|---|---|---|---|---|---|
| | | | Diethyl Amino | | |
| 4-Hydroxy-Pyridine | 11.2 | 7.5 | Ethylene Diamine | 10.2 | n 5 |
| 2-Hydroxy-Pyridine | 11.6 | 7.5 | Triethyl Amine | 10.8 | 5 |
| | | | Dimethyl Piperidine | 11.2 | 3 |

EXAMPLE 5

(pH Interval 2.5-5)

| Acid | pKa | c (mMol) | Base | pKa | c (mMol) |
|---|---|---|---|---|---|
| Citric Acid | 3.2 | 5 | Betaine | 1.8 | 20 |
| | | | 2-Amino Butyric | | |
| HIBA | 4.0 | 10 | Acid | 2.2 | 20 |
| Isobutyric Acid | 4.5 | 15 | Creatine | 2.7 | 15 |
| Picolinic Acid | 5.5 | 20 | Glycyl Glycine | 3.1 | 10 |
| | | | Pip.-4 Carboxylic | | |
| MES | 6.1 | 20 | Acid | 3.6 | 10 |
| | | | GABA | 4.2 | 5 |

In the specified media, mostly linear pH gradients are produced. The pH profile can be flattened in certain pH segments by modifying the relative concentrations of acids and bases. In the manufacture of the solutions in accordance with this invention, the order in which the individual compounds are added is usually irrelevant.

What is claimed is:

1. A medium for electrophoresis, comprising
   at least two acids whose pKa values are between approximately 3.0 and approximately 12, and
   at least two bases whose pKa values are between approximately 1.5 and approximately 11,
wherein for the majority of acids, an acid with a higher pKa value will have a higher relative and absolute concentration than an acid with a lower pKa value and wherein for the majority of bases, a base with a higher pKa value will have a lower relative and absolute concentration than a base with a lower pKa value.

2. The medium in accordance with claim 1, wherein for essentially all of the acids, an acid with a higher pKa value will have a higher relative and absolute concentration than an acid with a lower pKa value and wherein for the essentially all of the bases, a base with a higher pKa value will have a lower relative and absolute concentration than a base with a lower pKa value.

3. The medium in accordance with claim 1, wherein for all of the acids, an acid with a higher pKa value will have a higher relative and absolute concentration than an acid with a lower pKa value and wherein for all of the bases, a base with a higher pKa value will have a lower relative and absolute concentration than a base with a lower pKa value.

4. The medium in accordance with claim 1, wherein the medium contains at least three acids and at least three bases.

5. The medium in accordance with claim 1, wherein the concentrations of the individual acids and bases are selected to provide sufficient buffer capacity in a state of equilibrium upon completion of the electrophoretic migration.

6. The medium in accordance with claim 1, wherein, in order to establish narrower pH intervals, the absolute concentrations of the acids and bases are increased to achieve the narrower pH intervals.

7. The medium in accordance with claim 1, wherein, in order to establish narrower pH intervals, the ΔpKa values of the acids and bases are reduced through selection of the acids and bases to achieve the narrower pH intervals.

8. The medium in accordance with claim 1, wherein the molecular weights of both the acids and the bases used are less than 300 Dalton.

9. A medium for electrophoresis, comprising
   at least two acids whose pKa values are between approximately 3.0 and approximately 12, and
   at least two bases whose pKa values are between approximately 1.5 and approximately 11,
wherein the relative concentrations of the weaker acids are 1.5 to 3 times higher than that of the strongest acid when the difference between the pKa values of the strongest acid and the weaker acid is in the range from 1 to 3, the relative concentrations of the weaker acids are 4 to 8 times higher than that of the strongest acid when the difference between the pKa values of the strongest acid and the weaker acid is in the range from 3 to 8, the relative concentrations of the weaker bases are 1.5 to 3 times higher than that of the strongest base when the difference between the pKa values of the strongest base and the weaker base is in the range from 1 to 3, and the relative concentrations of the weaker bases are 4 to 8 times higher than that of the strongest base when the difference between the pKa values of the strongest base and the weaker base is in the range from 3 to 8.

10. The medium in accordance with claim 9, wherein the medium contains at least three acids and at least three bases.

11. The medium in accordance with claim 10, wherein ΔpKa of neighboring acids is not larger than 1, and wherein ΔpKa of neighboring bases is not larger than 1.

12. The medium in accordance with claim 11, wherein ΔpKa of neighboring acids is between 0.8 and 0.5.

13. The medium in accordance with claim 11, wherein ΔpKa of neighboring bases is between 0.8 and 0.5.

14. A medium for electrophoresis, comprising
   at least two acids whose pKa values are between approximately 3.0 and approximately 12, and
   at least two bases whose pKa values are between approximately 1.5 and approximately 11,
wherein for the majority of acids, an acid with a higher pKa value will have a higher relative and absolute concentration than an acid with a lower pKa value and wherein for the majority of bases, a base with a higher pKa value will have a lower relative and absolute concentration than a base with a lower pKa value,
wherein the relative concentrations of the weaker acids are 1.5 to 3 times higher than that of the strongest acid when the difference between the pKa values of the strongest acid and the weaker acid is in the range from 1 to 3, the relative concentrations of the weaker acids are 4 to 8 times higher than that of the strongest acid when the difference between the pKa values of the strongest acid and the weaker acid is in the range from 3 to 8, the relative concentrations of the weaker bases are 1.5 to 3 times higher than that of the strongest base when the difference between the pKa values of the strongest base and the weaker base is in the range from 1 to 3, and the relative concentrations of the weaker bases are 4 to 8 times higher than that of the strongest base when the difference between the pKa values of the strongest base and the weaker base is in the range from 3 to 8.

15. The medium in accordance with claim 14, wherein the medium contains at least three acids and at least three bases.

* * * * *